United States Patent [19]

Dryden

[11] Patent Number: 5,125,893
[45] Date of Patent: Jun. 30, 1992

[54] SUCTION CATHETER WITH WALL LUMEN FOR IRRIGATION

[76] Inventor: Gale E. Dryden, 5835 North Tacoma, Indianapolis, Ind. 46220

[21] Appl. No.: 509,232

[22] Filed: Apr. 16, 1990

[51] Int. Cl.⁵ .............................................. A61M 31/00
[52] U.S. Cl. ..................................... 604/54; 604/171; 128/207.14
[58] Field of Search ................ 604/171, 172, 263, 43, 604/45, 54; 128/207.14, 207.16

[56] References Cited

U.S. PATENT DOCUMENTS

| | | | |
|---|---|---|---|
| 3,902,500 | 9/1975 | Dryden | 604/171 X |
| 4,351,328 | 9/1982 | Bodai | 128/202.16 |
| 4,510,933 | 4/1985 | Wendt et al. | 128/207.14 |
| 4,805,611 | 2/1989 | Hodgkins | 128/207.14 |
| 4,838,255 | 6/1989 | Lambert | 128/202.16 |
| 4,850,350 | 7/1989 | Jackson | 128/207.16 |
| 4,872,579 | 10/1989 | Palmer | 128/205.19 |
| 4,881,542 | 11/1989 | Schmidt et al. | 128/207.14 |

Primary Examiner—John D. Yasko
Assistant Examiner—Adam J. Cermak
Attorney, Agent, or Firm—Woodard, Emhardt, Naughton, Moriarty & McNett

[57] ABSTRACT

One end of a tee adaptor connects to the proximal end of an endotracheal tube. The other end of the adaptor connects to one end of an elongate transparent flexible bag. The other end of the bag is attached to a catheter tube at a point remote from the adaptor and remote from the distal end of the catheter tube so the catheter tube is sheathed by the bag. A reed valve is between the distal end of the catheter tube and the adaptor connection to the endotracheal tube. The distal end of the catheter tube can be pushed through the reed valve and through the endotracheal tube into the lung for suctioning. The catheter tube has a lumen in its wall through which irrigation fluid is delivered to the distal end as suctioning occurs.

3 Claims, 2 Drawing Sheets

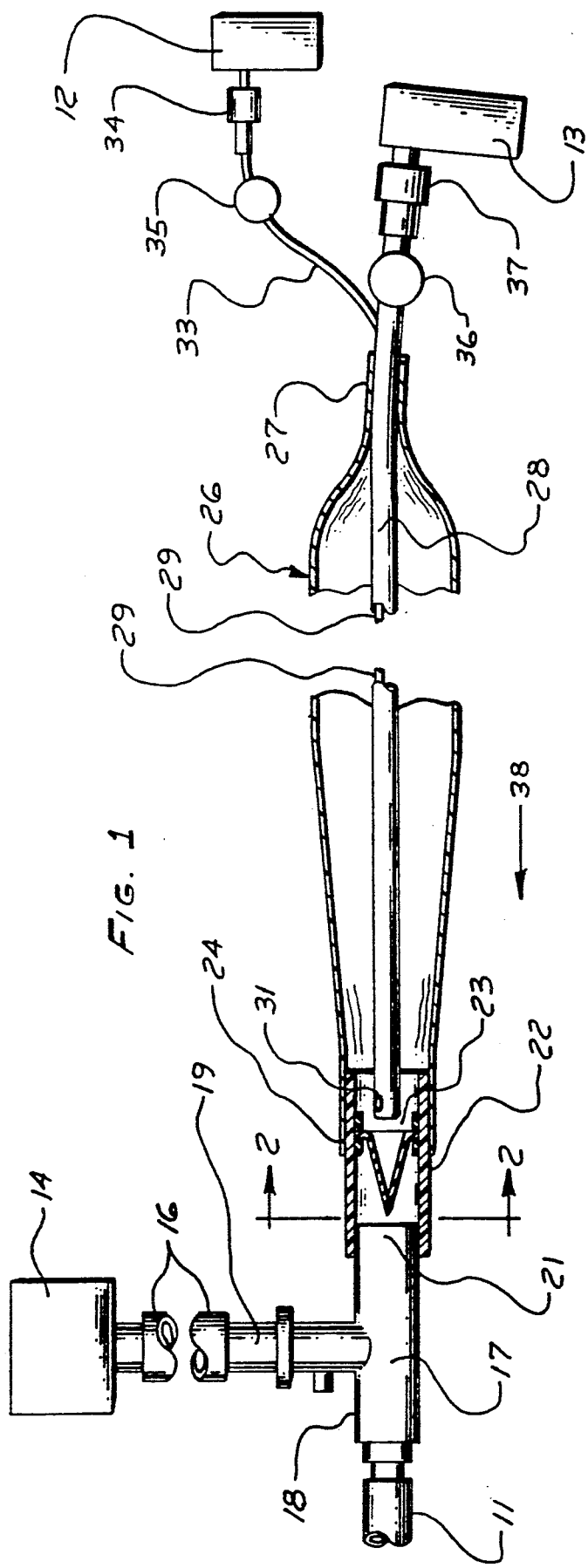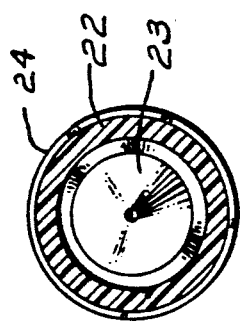

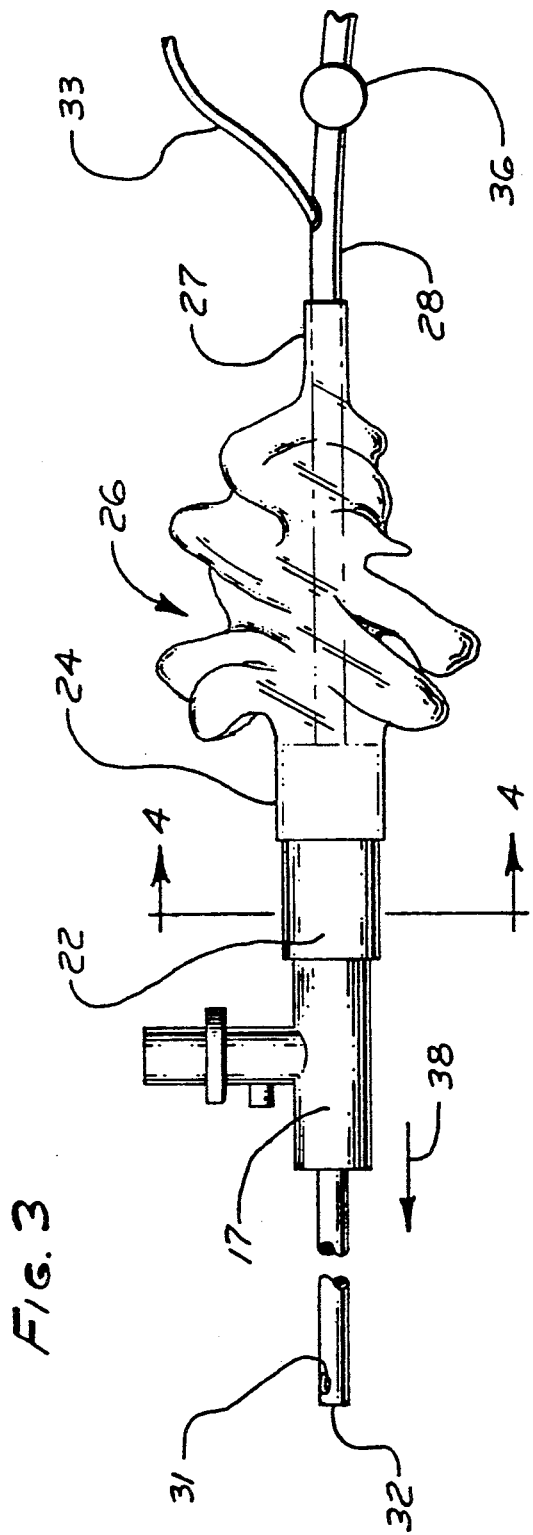
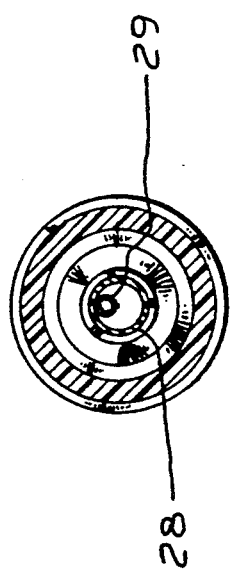
FIG. 3
FIG. 4

SUCTION CATHETER WITH WALL LUMEN FOR IRRIGATION

BACKGROUND OF THE INVENTION

1. Field of the Invention

This invention relates generally to endotracheal catheters, and more particularly to a suction catheter with internal irrigation feature.

2. Description of the Prior Art

U.S. Pat. No. 3,902,500 issued to me on Sep. 2, 1975 disclosed an endotracheal catheter apparatus including a fitting connectable to an endotracheal tube to facilitate supply of air while the catheter apparatus is attached. A bag connected to the fitting surrounds a catheter tube and enables a person to advance the catheter down through the endotracheal tube without touching the catheter tube itself, thus contributing to a sterile technique. That apparatus has served its purpose very well.

It is sometimes necessary to provide irrigation in the lung to enable effective suctioning. The present invention is directed to effective irrigation.

SUMMARY OF THE INVENTION

Described briefly, according to a typical embodiment of the present invention, a suction catheter assembly has an adaptor for connection to the proximal end of an endotracheal tube to facilitate the supply of oxygen or air through the tube during catheterization. One end of an elongate transparent flexible bag is attached to the adaptor. The other end of the bag is attached to a catheter tube at a point remote from the adaptor. The catheter tube has a distal end adjacent the adaptor. A valve is provided adjacent the adaptor between the distal end of the catheter tube and the point of connection to the endotracheal tube. The catheter tube has a lumen in its wall through which irrigation fluid is passed if needed to dilute the lung secretions as suctioning occurs through the catheter after the catheter has been advanced through the valve, adaptor and endotracheal tube into the lung. The distal tip of the catheter is softened to reduce mechanical trauma to the lung airway. The sleeve bag can inflate during the catheterization procedure to facilitate addition of oxygen or an oxygen/air mixture to the lungs by squeezing the bag after suctioning. The sleeve bag also monitors the presence of adequate gas volume to prevent over suction which can result in lung collapse. The valve can be used to prevent the sleeve from inflating while getting the tube down. Then the valve can be open for suctioning. Alternatively, input air volume into the sleeve can be controlled through the adaptor, thus reducing the problem of the bag inflating to such an extent as to unintentionally withdraw the catheter.

BRIEF DESCRIPTION OF THE DRAWINGS

FIG. 1 is a side elevational view, partially in section, showing a catheter apparatus according to a typical embodiment of the present invention.

FIG. 2 is a cross-section therethrough taken at line 2—2 in FIG. 1 and viewed in the direction of the arrows.

FIG. 3 is an elevational view showing the catheter tube extended through the end of the adaptor as is done during catheterization.

FIG. 4 is a section taken at line 4—4 in FIG. 3 and viewed in the direction of the arrows.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, the proximal end of an endotracheal tube is shown at 11. An irrigation fluid supply is shown at 12, and a suction machine is shown at 13. An air/oxygen supplying ventilator machine is shown at 14. An adaptor tee 17 has one end portion 18 coupled through a step-down adaptor to the endotracheal tube. The branch portion 19 of fitting 17 is coupled through tube 16 to the machine 14. The other end 21 of the fitting is connected to a sleeve 22 having a valve 23 therein. The sleeve also has one end 24 of a flexible transparent sheath 26 attached and sealed to it. The other end portion 27 of the sheath is connected and sealed to the catheter tube 28 which has a lumen 29 in its wall. The in-the-wall lumen has an outlet port 31 at its distal end adjacent the distal end 32 of the catheter tube. Where the catheter is broken apart in the middle of FIG. 1 to conserve space in the drawing, the lumen 29 is shown as a stub end but this is only for descriptive purposes to show continuity, since the lumen may actually be formed in the wall of the catheter and is not necessarily a separate tube. However, the proximal end of the lumen is connected to a tube 33 connected by a suitable fitting 34 to the source 12 of irrigation fluid. The catheter tube itself is connected through a valve 36 and fitting 37 to the suction machine 13. It should be understood that, in these figures, the lengths of these tubes and the sizes of the associated machines 12, 13 and 14 are not at all to scale.

When it is desired to do suctioning, the adaptor 17 may be held in one hand and the catheter tube advanced to the left in the direction of arrow 38 through the valve 23 and fitting 17 and endotracheal tube until its distal end is in the lung area where secretions are to be removed. The amount of vacuum applied can be controlled by the valve 36. This can be a conventional roller valve of the type used on intravenous feeding tubes. Other valve types might be used. Another example is the squeeze-to-open, automatic-closure, type. Similarly, the amount of irrigation fluid supplied can be controlled by valve 35.

A breathing mixture from a ventilating apparatus 14 or other source can continue to be supplied through the tee 17 and therefrom through the endotracheal tube into the lung. Since the valve 23 is a reed-type valve or may be an iris valve, very little leakage in a direction opposite arrow 38 into the bag 26 will occur. So there is no difficulty with the bag trying to inflate and pull the catheter out. The sleeve wall 22 is not rigid. Therefore, the wall can be compressed by squeezing it to open the valve 23 and admit breathing mixture to the bag 26, if desired, either during or after the catheterization. In this way, the sheath 26 can be inflated with the breathing mixture and can be observed by a person and thereby used to indicate excess suctioning that could cause lung collapse. The sheath 26 may also be compressed by hand to introduce a surge of air or oxygen into the lungs if and when desired.

The valve 23 can be either a reed-type of valve and which can be opened by squeezing the wall of the sleeve 22, or it can be a rotary valve which can be opened and closed by rotation of a part of the valve in the sleeve, or a sleeve valve which can be operated by sliding a part of it to open an aperture.

The materials, dimensions and volumes can be essentially the same as in the above-mentioned patent.

The present invention still permits monitoring of gas volume removed by the suction flow, thus helping control vacuum to prevent removing the functional volume of the lungs and cause hypoxia and atelectasis. The application of the irrigation fluid directly to the tip of the catheter where the secretions are, reduces the volume of irrigation needed to help clear thick secretions in the lung and clean the catheter after use. The valve 23 at the proximal end of the tee fitting, when closed, will help pool the irrigation solution when clearing the catheter after use. When the catheter is extended through the valve, air can gradually fill the bag 26 so observation of adequate air volume suction is possible. If a rotary valve or sliding valve is used at the sleeve 22, the valve can be rotated to open position and the bag can be used if needed for manual ventilation.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of facilitating operation of a suction catheter and comprising the steps of:
    advancing a double lumen suction catheter from a catheter enclosing bag through a valve and a breathing tube adaptor;
    supplying oxygen through the adaptor to a breathing tube;
    providing sufficient sealing between the catheter and the valve to prevent the bag from over inflating and pulling the catheter out of the adaptor;
    admitting some oxygen through the valve into the bag; and
    flowing an irrigating fluid out of a distal end portion of the catheter while simultaneously inducing a flow of material into an inlet in said catheter end portion;
    observing the bag while inducing the flow, to identify excess suctioning that could cause lung collapse.

2. The method of claim 1 wherein:
    the flow of fluid is directed out the side of the catheter end portion while the flow of material is induced into the end of the end portion.

3. A method of facilitating operation of a suction catheter and comprising the steps of:
    flowing an irrigating fluid out of a distal end portion of a suction catheter while inducing a flow of material into an inlet in said catheter end portion; and
    pooling the material and irrigating fluid about a valve in a catheter sheath assembly while flowing and inducing flow.

* * * * *